(12) United States Patent
Whitin et al.

(10) Patent No.: US 6,190,396 B1
(45) Date of Patent: Feb. 20, 2001

(54) DEVICE AND METHOD FOR DEPLOYING AND ORGANIZING SUTURES FOR ANASTOMOTIC AND OTHER ATTACHMENTS

(75) Inventors: Kate Whitin, San Mateo; Lewis Isbell, Santa Clara, both of CA (US)

(73) Assignee: Perclose, Inc., Redwood City, CA (US)

( * ) Notice: Under 35 U.S.C. 154(b), the term of this patent shall be extended for 0 days.

(21) Appl. No.: 09/395,921

(22) Filed: Sep. 14, 1999

(51) Int. Cl.$^7$ .................................................. A61B 17/04
(52) U.S. Cl. ........................... 606/144; 606/139; 606/148
(58) Field of Search .................... 606/144, 152, 606/153, 139, 147, 148

(56) References Cited

U.S. PATENT DOCUMENTS

| | | |
|---|---|---|
| 312,408 | 2/1885 | Wacker Hagen . |
| D. 372,310 | 7/1996 | Harnett . |
| 659,422 | 10/1900 | Shidler . |
| 2,397,823 | 4/1946 | Walter . |
| 2,646,045 | 7/1953 | Priestly . |
| 2,959,172 | 11/1960 | Held . |

(List continued on next page.)

FOREIGN PATENT DOCUMENTS

| | | |
|---|---|---|
| 4210724 C1 | 7/1983 | (DE) . |
| 01407557A | 5/1985 | (EP) . |
| 0474 887 A1 | 3/1992 | (EP) . |
| 0478 358 A1 | 4/1992 | (EP) . |
| 0589 409 A1 | 9/1992 | (EP) . |
| 0624 343 A2 | 4/1993 | (EP) . |
| 0542 126 A3 | 5/1993 | (EP) . |
| 0568 098 A2 | 11/1993 | (EP) . |
| 405042161 | 2/1993 | (JP) . |
| 993922 | 2/1983 | (SU) . |
| 1093 329A | 5/1984 | (SU) . |
| 1174 036A | 8/1985 | (SU) . |
| 1648400 | 5/1991 | (SU) . |
| 820810 | 6/1997 | (SU) . |
| WO 94/27503 | 6/1993 | (WO) . |
| WO 94/28801 | 6/1993 | (WO) . |
| WO 95/05121 | 8/1993 | (WO) . |
| 9405213 | 3/1994 | (WO) . |
| WO 95/35065 | 2/1995 | (WO) . |

OTHER PUBLICATIONS

Eligloy Brochure, Elgin National Watch Co., Elgin, IL. (Jun. 23, 1959).
Product Brochure "The Proven Solution to Endoscopic Suturing", Laurus Medical Corp, Irvine, CA. (Oct. 1994).
Datascope Corporation, Montvale, NJ, American Heart Assoc. Meeting, Anaheim, 1 page, (1991).

(List continued on next page.)

*Primary Examiner*—Gary Jackson
(74) *Attorney, Agent, or Firm*—Townsend and Townsend and Crew LLP (57) ABSTRACT

Devices, methods, and kits are provided for use with a body duct. More specifically, a device is provided for positioning sutures through a body duct. The device comprises a shaft structure for holding the end of the body duct and a suture organizer mounted about the structure. A plurality of needles are arranged on the shaft structure where each of the needles are advanced along a path in radially outward direction from the shaft structure through the end of the body duct and into a suture organizer. The suture organizer is movable relative to the shaft structure. Preferably, but not necessarily, moving the suture organizer extends the sutures from the body duct. Preferably, after the sutures have been positioned through the body duct, they may be tied off with sutures from a target body duct or tissue, where the tying off of the sutures will join the body duct to the targeted area. The suture organizer can hold the needle and sutures to facilitate the tying off of individual sutures. The present invention preferably allows for the placement of sutures in the body duct in an evenly spaced radial pattern at a specified distance from the end of the body duct.

39 Claims, 6 Drawing Sheets

U.S. PATENT DOCUMENTS

| | | |
|---|---|---|
| 3,104,666 | 9/1963 | Hale et al. . |
| 3,470,875 | 10/1969 | Johnson . |
| 3,653,388 | 4/1972 | Tenckhoff . |
| 3,665,926 | 5/1972 | Flores . |
| 3,776,237 | 12/1973 | Hill et al. . |
| 3,820,544 | 6/1974 | Semm . |
| 3,926,194 | 12/1975 | Greenberg et al. . |
| 3,939,820 | 2/1976 | Grayzel . |
| 4,018,228 | 4/1977 | Goosen . |
| 4,109,658 | 8/1978 | Hughes . |
| 4,161,951 | 7/1979 | Scanlan, Jr. . |
| 4,168,073 | 9/1979 | LaRue . |
| 4,216,776 | 8/1980 | Downie et al. . |
| 4,235,177 | 11/1980 | Arbuckle . |
| 4,317,445 | 3/1982 | Robinson . |
| 4,411,654 | 10/1983 | Boarini et al. . |
| 4,412,832 | 11/1983 | King et al. . |
| 4,437,465 | 3/1984 | Nomoto et al. . |
| 4,493,323 | 1/1985 | Albright et al. . |
| 4,553,543 * | 11/1985 | Amarasinghe ................... 606/153 |
| 4,587,969 | 5/1986 | Gillis . |
| 4,596,559 | 6/1986 | Fleishhacker . |
| 4,629,450 | 12/1986 | Suzuki et al. . |
| 4,738,666 | 4/1988 | Fuqua ............................. 604/280 |
| 4,744,364 | 5/1988 | Kensey . |
| 4,836,205 | 6/1989 | Barrett . |
| 4,852,568 | 8/1989 | Kensey . |
| 4,890,612 | 1/1990 | Kensey . |
| 4,898,155 | 2/1990 | Ovil et al. . |
| 4,911,164 | 3/1990 | Roth . |
| 4,926,860 | 5/1990 | Stice et al. . |
| 4,929,246 | 5/1990 | Sinofsky . |
| 4,935,027 | 6/1990 | Yoon . |
| 4,957,498 | 9/1990 | Caspari et al. . |
| 4,983,168 | 1/1991 | Moorehead . |
| 4,984,581 | 1/1991 | Stice . |
| 5,002,563 | 3/1991 | Pyka et al. . |
| 5,009,643 | 4/1991 | Reich et al. . |
| 5,021,059 | 6/1991 | Kensey et al. . |
| 5,037,433 | 8/1991 | Wilk et al. . |
| 5,047,039 | 9/1991 | Avant et al. . |
| 5,059,201 | 10/1991 | Asnis . |
| 5,061,274 | 10/1991 | Kensey . |
| 5,100,419 | 3/1992 | Ehlers . |
| 5,100,432 | 3/1992 | Matsutani . |
| 5,109,780 | 5/1992 | Slouf et al. . |
| 5,129,913 | 7/1992 | Ruppert . |
| 5,147,373 | 9/1992 | Ferzli . |
| 5,160,339 | 11/1992 | Chen et al. . |
| 5,171,251 | 12/1992 | Bregen et al. . |
| 5,192,294 | 3/1993 | Blake, III . |
| 5,192,302 | 3/1993 | Kensey et al. . |
| 5,219,358 | 6/1993 | Bendel et al. . |
| 5,222,974 | 6/1993 | Kensey et al. . |
| 5,234,443 | 8/1993 | Phan et al. . |
| 5,242,427 | 9/1993 | Bilweis . |
| 5,250,033 | 10/1993 | Evans et al. . |
| 5,250,053 | 10/1993 | Snyder . |
| 5,254,126 | 10/1993 | Filipi et al. . |
| 5,258,003 | 11/1993 | Ciaglia et al. . |
| 5,279,311 | 1/1994 | Synder . |
| 5,289,963 | 3/1994 | McGarry . |
| 5,290,284 | 3/1994 | Adair . |
| 5,290,297 | 3/1994 | Phillips . |
| 5,293,881 | 3/1994 | Green et al. . |
| 5,295,993 | 3/1994 | Green . |
| 5,300,085 | 4/1994 | Yock . |
| 5,304,184 | 4/1994 | Hathaway . |
| 5,304,185 | 4/1994 | Taylor . |
| 5,306,254 | 4/1994 | Nash et al. . |
| 5,320,632 | 6/1994 | Heidmueller . |
| 5,336,230 | 8/1994 | Leichtling et al. . |
| 5,336,231 | 8/1994 | Adair . |
| 5,342,369 | 8/1994 | Harryman, II . |
| 5,364,408 | 11/1994 | Gordon . |
| 5,368,601 | 11/1994 | Saver et al. . |
| 5,374,275 | 12/1994 | Bradley et al. . |
| 5,387,221 | 2/1995 | Bisgaard . |
| 5,387,227 | 2/1995 | Grice . |
| 5,395,349 | 3/1995 | Quiachon et al. . |
| 5,397,325 | 3/1995 | Della Badia et al. . |
| 5,403,329 | 4/1995 | Hinchcliffe . |
| 5,403,338 | 4/1995 | Milo . |
| 5,411,481 | 5/1995 | Allen et al. . |
| 5,417,699 | 5/1995 | Klein et al. . |
| 5,425,705 | 6/1995 | Evard et al. . |
| 5,431,666 | 7/1995 | Sauer et al. .................... 606/139 |
| 5,433,700 | 7/1995 | Peters . |
| 5,452,733 | 9/1995 | Sterman et al. . |
| 5,454,834 | 10/1995 | Boebel et al. . |
| 5,458,574 | 10/1995 | Machold et al. . |
| 5,476,469 | 12/1995 | Hathaway . |
| 5,478,309 | 12/1995 | Sweezer et al. . |
| 5,486,190 | 1/1996 | Green . |
| 5,489,295 | 2/1996 | Piplani et al. .................... 623/1 |
| 5,496,332 | 3/1996 | Sierra et al. . |
| 5,507,744 | 4/1996 | Tay et al. . |
| 5,507,755 | 4/1996 | Gresl et al. . |
| 5,507,757 | 4/1996 | Sauer et al. . |
| 5,509,902 | 4/1996 | Raulerson . |
| 5,520,665 | 5/1996 | Davila et al. . |
| 5,527,322 | 6/1996 | Klein et al. . |
| 5,540,704 | 7/1996 | Gordon et al. . |
| 5,545,171 | 8/1996 | Sharkey et al. . |
| 5,545,178 | 8/1996 | Kensey et al. . |
| 5,545,180 | 8/1996 | Le et al. . |
| 5,554,162 * | 9/1996 | DeLange ....................... 606/153 |
| 5,562,686 | 10/1996 | Sauer et al. ................... 606/144 |
| 5,562,728 | 10/1996 | Lazarus et al. .................. 623/1 |
| 5,573,540 | 11/1996 | Yoon . |
| 5,591,179 | 1/1997 | Edelstein . |
| 5,591,206 | 1/1997 | Moufarrege . |
| 5,611,794 | 3/1997 | Sauer et al. . |
| 5,613,975 | 3/1997 | Christy . |
| 5,836,956 | 11/1998 | Buelna et al. .................. 606/148 |
| 5,846,253 | 12/1998 | Buelna et al. .................. 606/148 |

OTHER PUBLICATIONS

Kensey Nash Corporation, Exton, PA, "The Hemostatic Puncture Closure Device", 2 pages.

"Innovation Through Progress", REMA–Medizintechnik, GMBH, Jan. 1992.

AD: The laurus In–Line Endoscopic Suturing Device (The Laurus ND–2600 Needle Driver), Laurus Medical Corp., Rev. Oct. 1994.

Cardiac Catheterization and Angiography, 3rd Ed., Lea & Fabiger, Philadelphia, 1986.

Cardio–Thoracic Systems Prospectus dated Mar. 20, 1996.

* cited by examiner

DEVICE AND METHOD FOR DEPLOYING AND ORGANIZING SUTURES FOR ANASTOMOTIC AND OTHER ATTACHMENTS

CROSS-REFERENCES TO RELATED APPLICATIONS

The present application is related to commonly assigned, copending U.S. patent application Ser. No. 08/824,031 filed on Mar. 26, 1997, U.S. Pat. No. 6,036,699 Ser. No. 08/883, 246 pending filed on Jun. 26, 1997, and Ser. No. 09/395,901 filed on the same day as the present application. The full disclosures of each of these applications are incorporated herein by reference.

BACKGROUND OF THE INVENTION

The present invention relates generally to devices and methods for suturing body tissue. More particularly, the present invention is useful for performing end-to-side and end-to-end attachments of body ducts, such as in suturing coronary blood vessel grafts.

In many medical procedures today, it is desirable to connect a body duct, such as a hollow organ or blood vessel, to a targeted piece of tissue. In coronary surgery, this type of attachment is commonly referred to as an anastomosis. In coronary artery bypass graft surgery ("CABG"), a graft blood vessel may be anastomosized to an arterial wall of an artery to supply blood downstream of a blockage in another blood vessel. The proximal end of the blood vessel graft is typically connected to a pressurized arterial blood supply, such as the aorta, while the distal end is coupled to the vessel lumen downstream of the blockage. The amount of time spent performing these anastomosis procedures to connect blood vessel grafts between blocked arteries and pressurized blood supplies is critical to patient mortality and morbidity. In conventional CABG surgery, three critical determinates that affect the outcome of a bypass surgery are (1) time the patient spends on cardiopulmonary bypass, (2) time the patient spends with a clamped aorta, and (3) the quality of the anastomosis. It is generally understood that the risk of patient morbidity rises significantly after a threshold time of one hour on cardiopulmonary bypass. Continual circulation of blood through the mechanical apparatus of the bypass machine can cause various degradations to the blood. Perhaps the most prevalent complication arising from prolonged cardiac bypass is the high risk of distal thrombosis, which can embolize in the neurovasculature and potentially cause a stroke.

A critical factor in reducing the amount of time a patient spends on bypass is directly related to the time spent anastomosing the blood vessel grafts used during surgery. The average time for suturing one anastomosis is approximately seven to ten minutes. It is believed that an average CABG procedure involves approximately five anastomoses. Therefore, the average time for graft suturing ranges from thirty-five to fifty minutes, which is a significant portion of the sixty-minute threshold for patient morbidity. Patients treated with conventional coronary surgery and placed on cardiopulmonary bypass would benefit from reducing the amount of time spent performing each anastomosis.

In "off pump" procedures where patients are not placed on cardiopulmonary bypass and the heart remains beating, the difficulty of suturing an anastomosis graft on a moving surface of the heart may degrade the quality of such grafts completed on patients. "Off pump" procedures do not use cardiopulmonary bypass pumps or devices and thus reduces the blood damage associated with bypass devices. "Off pump" procedures, however, require a higher degree of expertise to perform coronary artery bypass grafts on a beating or moving object. An anastomosis differs from straight line suturing in that each suture has a different orientation that is based on its position around the cross-sectional circumference of the blood vessel graft. It can be appreciated that some of the sutures are easily made from on top of the conduit or blood vessel graft, while others are more difficult to complete as they are beneath the conduit. It can be further appreciated that performing such complex suturing procedures on a moving platform, such as the beating heart, further increases the difficulty associated with such suturing procedures. Improperly connecting blood vessel grafts to the patient may present substantial postoperative complications and/or increase operating room time spent correcting the improperly connected graft.

Accordingly, it would be desirable to provide improved devices and methods that simplify anastomosis graft procedures performed on patients, particularly where multiple graft procedures are to be performed. Simplifying the anastomosis procedure would typically reduce the time spent on each graft and thus minimize the time a patient spends on cardiopulmonary bypass. Additionally, it would be desirable to provide a device that improves the consistency of the suture pattern created during each anastomosis graft.

SUMMARY OF THE INVENTION

The present invention comprises devices, methods, and kits for use with a body duct. The present invention improves and simplifies suture placement through the body duct is particularly useful for placing multiple sutures in the end of a body duct in a manner which is useful for forming an anastomotic attachment to the side or end of another body duct. The present invention is particularly useful in performing anastomotic attachments as part of coronary artery bypass grafting (CABG) procedures in a variety of environments including to both stopped heart and beating heart procedures. The present invention may be used in open surgical procedures as well as in minimally invasive procedures using percutaneous access such those developed by Heartport, Inc. of Redwood City, Calif. and by CardioThoracic Systems, Inc. of Cupertino, Calif.

The present invention preferably provides for the delivery of a plurality of needles through the body duct in a single continuous motion by the user. Advantageously, this simplified needle delivery reduces the overall amount of time spent on performing a body duct connection such as an anastomosis. Although not limited in this manner, the invention provides for rapid and consistent placement of both needles and sutures through the body duct. The present invention preferably allows the sutures to be easily organized to facilitate the tying off of the sutures during an anastomosis procedure. In situations where the invention is used with a beating heart, the invention allows for rapid actuation once the device is properly positioned, reducing the likelihood that movement of the beating heart may misposition the device during actuation. The present invention further allows for the simultaneous delivery of a plurality of needles through the body duct in a desired pattern, typically in an evenly-spaced manner, which thus improves the quality of the anastomosis by having a consistent suture pattern and a calculated tissue capture.

In one aspect of the present invention, a device is provided for use with a body duct. The device of the present invention comprises a shaft structure for holding the end of the body duct on a portion of the structure and a suture organizer mounted about the shaft structure. A plurality of needles are arranged on the shaft structure where each of the needles can be advanced along a path in a radially outward direction from the shaft structure, through the end of the body duct, and into a suture organizer. The suture organizer is preferably movable relative to the shaft structure so that the organizer can be moved away from the shaft structure to facilitate placement of the body duct over the structure. The suture organizer can then be moved back into place over the body duct to be in position to receive the needles and/or suture, as described in more detail below. After capturing the needles/suture, the suture organizer can then be moved or removed from the shaft to permit access to the suture ends which are to be tied off. Typically, after the sutures have been positioned through the body duct, they may be tied off with sutures from a target body duct or tissue, where the tying off of the sutures will join the body duct to the targeted area. The suture organizer can hold the needle and sutures to facilitate the tying off of individual sutures. The present invention preferably allows for the placement of sutures in the body duct in a pre-determined pattern, usually an evenly spaced radial pattern, at a specified distance from the end of the body duct.

In one embodiment of the invention, the suture organizer is designed to mate with another suture organizer containing sutures attached to a target tissue to facilitate connection of the body duct to the target tissue. The suture organizer may have an engaging surface or similar structure to allow mating of the organizers. Typically, mating the portions of the suture organizer will facilitate the mapping of the sutures from different suture organizer portions. Typically, the suture organizer will be moved to mate with the other suture organizer portions. The suture organizer may be moveable while attached to the apparatus, or in some embodiments, may be completely removed from the apparatus to facilitate mapping of the sutures.

When pairs of suture organizers are used, each organizer will typically be attached to opposite ends of common groups of sutures. While in some instances it may be desirable to tie-off separate lengths of sutures for various purposes, it will be far more common to tie-off opposite ends of single suture lengths in order to attach tissue, close wounds, etc. When handling pluralities of suture lengths, the need to track and identify individual sutures so that the appropriate suture ends can be tied together can be quite challenging. The present invention addresses this challenge by capturing at least a first group of suture ends in a first organizer and optionally capturing the second ends of the same sutures in a second organizer. By then appropriately aligning the two organizers, optionally including attaching portions of the organizers together, the suture ends will be arranged in a fashion which permits easy access to the particular ends which are to be tied together.

The suture organizer preferably has a soft material insert made of a material such as a polymer or silicone for receiving and holding needles inserted therein. The material insert preferably has a thickness sufficient to substantially contain the needles therein. Needles substantially embedded in the suture organizer are more easily retained therein. The suture organizer is adapted to hold said needles after the needles are removed from the shaft structure and may be mounted in a needle receiving position about the body duct when the body duct is on the shaft structure. Preferably, but not necessarily, the needles are maintained in a substantially fixed configuration after the needles are removed from the shaft structure. This organizes the attached sutures to facilitate the tying off of the individual sutures.

The suture organizer may be made of a plurality of portions. In one embodiment, the suture organizer may have a first breakaway portion and a second breakaway portion where the portions are separable. Although not limited in this manner, each portion may then be coupled or mated to another suture organizer carrying other sutures. The portions may be coupled together using a variety of releasable connection devices such as hook and loop fasteners (e.g., Velcro®), ratcheting ties, snaps, elastic loops, banded clips, pre-tied suture knots, and the like. The needles are typically arranged on the shaft structure to deploy in an evenly spaced radial pattern. This facilitates a consistent tissue capture for the suturing device. The radial pattern will typically be arranged so that the needle tips deploy in an annular fashion consistent with a "straight" cut body lumen. The pattern can also be shifted or inclined relative to the axis of the shaft structure.

While the suture organizers will typically be adapted to capture needles which carry suture ends, the present invention also covers devices and methods where the suture organizers directly capture suture. For example, a needle which is used to penetrate the tissue duct may carry the suture in such a manner that the suture organizer will capture only the suture, leaving the needle free to be proximally withdrawn back through the tissue. Capture of the suture directly, rather than the needle which carries the suture, can eliminate the need for the surgeon to remove the suture from the needle prior to tying.

The present invention will also include needles and drivers which carry separate pluralities of needles capable of separate deployment. Usually, such separate needle pluralities will be connected to opposite ends of individual suture lengths so that the same needle driver can be used to first deploy one group of suture ends through a first tissue target site and then deploy a second group of suture ends through a second tissue target site. By then applying the suture organizers, the opposite ends of the suture lengths can be captured and rearranged to facilitate tying of the individual sutures. While the specific embodiments illustrated hereinafter generally show only a first needle driving mechanism suitable for manipulating a first group of the needles and suture ends, it will be appreciated that an identical structure can be provided on another portion or end of the device to permit deployment of both hands of the suture pluralities in a given suture attachment protocol, e.g., an end-to-end anastomotic attachment of body duct ends.

In another aspect of the present invention, a method is provided for placing a plurality of sutures through a body duct using a suturing device having a shaft structure. Although not limited in this manner, such suturing is particularly suited for performing an anastomosis graft during coronary surgery. The method involves positioning an end of the body duct over the shaft structure of the suturing device. A plurality of needles each carrying a suture are advanced radially outwardly from the shaft structure, radially outwardly through the end of the body duct, and into a suture organizer. The suture organizer may be moved to extend the sutures between the needles in the suture organizer and the body duct. Typically, the suture organizer is mated to another suture organizer having a plurality of corresponding sutures to facilitate the tying off of the sutures. Tying off of the sutures brings the body duct in contact with a target tissue. Preferably, but not necessarily, the needles are maintained in a substantially fixed configuration by the suture organizer after the needles are removed from the shaft structure. This organizes the attached sutures to facilitate the tying off of the individual sutures. Typically, the needles are advanced by a plunger which pushes the plurality of needles through needle channels in the shaft structure. The suture organizer may also be used to clamp the body duct to the shaft structure. The suture organizer will usually define a ring having a plane perpendicular to the axis of the shaft structure. Alternatively, the needle tips and suture organizer can be inclined or angled relative to the axis of the shaft to accommodate various angled grafts, i.e., those which are cut at an angle at the end to be sutured.

The present invention still further provides methods for suturing tissue locations together. The tissue locations will typically include at least one body duct and will more usually comprise two body ducts which are being connected in an end-to-end anastomosis, end-to-side anastomosis, or side-to-side anastomosis. A plurality of suture lengths are provided, typically having needles connected at each end. The first ends of the suture lengths are then penetrated in a pre-determined pattern at a first tissue location, such as at the end or in a side of a body duct. The first suture ends are then captured in a first suture organizer, typically by penetrating needles into a soft material as described above. Alternatively, the sutures can be captured directly and removed from the penetrating needles as part of the suture capture. The second ends of the suture lengths are penetrated in a predetermined pattern at a second tissue location which may be the end of a body duct, the side of a body duct, or elsewhere. The second suture ends are captured in a second suture organizer, and the first suture organizer and second suture organizer are positioned relative to each other in a manner which will facilitate organization of the multiple suture ends. Typically, the first and second ends of each individual suture length are positioned adjacent one another so that it is immediately apparent to the surgeon which sutures are to be secured. The first and second ends of at least some of the sutures are then secured to each other, typically by tying, fusing, clipping, or other conventional suture attachment techniques.

Kits according to the present invention will comprise a graft suturing device which delivers a plurality of needles. The kits will further include instructions for use setting forth a method as described above. Optionally, the kits will further include packaging suitable for containing the graft device and the instructions for use. Exemplary containers include pouches, trays, boxes, tubes, and the like. The instructions for use may be provided on a separate sheet of paper or other medium. Optionally, the instructions may be printed in whole or in part on the packaging. Usually, at least the graft suturing device will be provided in a sterilized condition. Other kit components, such as the graft to be sutured, may also be included.

A further understanding of the nature and advantages of the invention will become apparent by reference to the remaining portions of the specification and drawings.

DESCRIPTION OF THE SPECIFIC EMBODIMENTS

The present invention is directed towards devices, methods, and kits for facilitating the delivery of sutures through a body duct. Although applicable to a variety of surgical environments, the present invention has particular application to coronary heart surgery. The device of the present invention may be used with other suture devices to perform end-to-side or end-to-end anastomosis.

As described below, devices of the present invention can preferably deploy a plurality of needles in an evenly spaced or otherwise predetermined configuration through a body duct to perform an anastomosis. In preferred embodiments, a device of the present invention can position the suture for performing the end-to-side anastomosis through one hand stroke or motion by the user. Deployment of a plurality of needles in a predetermined pattern increases the likelihood that that the anastomosis will have sufficient patency to channel blood as desired and have reduced incidence of fluid leakage. More importantly, however, the present device will reduce the amount of time a patient spends on a cardiopulmonary bypass, which has a direct relationship to a patient's operative and peri-operative morbidity. In preferred embodiments, the present invention advantageously facilitates the tying off of the sutures in the body duct by organizing the sutures after they have been delivered through the duct. The reduced number of steps required for a user to perform an anastomosis lends the present device for use in beating heart or off-pump procedures.

The term "body duct" as used herein is generally in reference to a blood vessel. It should be understood, however, that the term is intended to cover a variety of body lumens and may refer to non-vascular body lumens such as the bile duct, the urethra, the urinary bladder, or other body lumens which require assistance to be rejoined. Typically target blood vessels and graft vessels include internal mammary arteries (IMA's), saphenous veins, radial arteries, coronary arteries, synthetic grafts, and the like.

The present invention is particularly useful in attaching a tubular graft to the side of another tissue structure or to the end of another tissue structure. Preferably, but not necessarily, the device of the present invention is used to deliver one end of a suture through a tubular body graft while the other end of the suture is delivered through tissue of another tissue structure using other needle delivery devices or methods. These suture ends may be brought together and tied off to secure the tubular body graft or body duct to the target tissue. As will be described in further detail below, the needles are delivered along a path in a radially outward direction from the shaft structure and outwardly through the end of the body duct into a suture organizer. Preferably, the needles advanced along the path are maintained in a fixed configuration relative to one another once they enter the suture organizer and are removed outwardly from the body duct. Typically, maintaining the needles in a fixed configuration organizes the sutures and will reduce the amount of the time needed to individually tie off the ends of the sutures.

Figure 1:
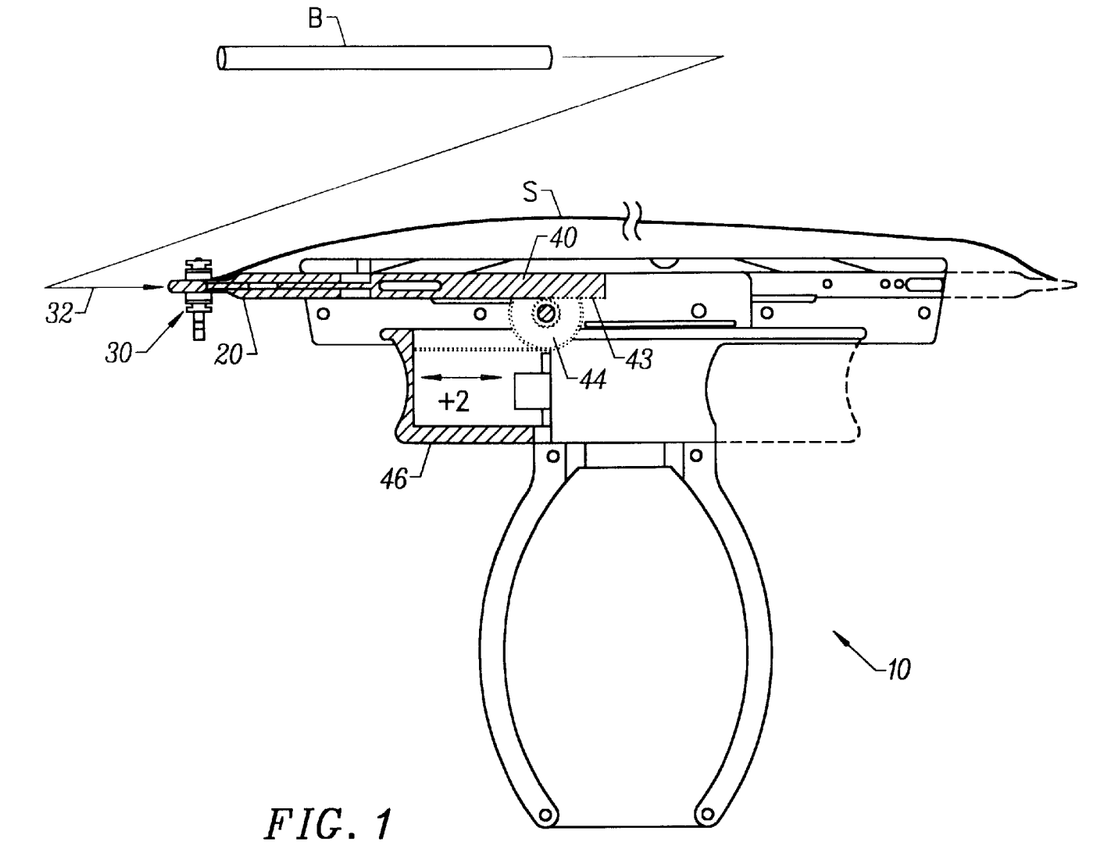
FIG. 1 shows a cross-section of a preferred embodiment of the apparatus according to the present invention.

Referring now to FIG. 1, a needle driving device or driver 10 according to the present invention will be described in further detail. FIG. 1 shows a cross-section of the needle driving device 10. The device 10 is used to position sutures and suture ends through a body duct B that can be mounted on a shaft structure 20 of the device. The device 10 includes a suture organizer 30 which, in the embodiment shown, comprises a cylindrical-shaped clamp having an opening through the center which may be used to surround the body duct B when the duct is mounted at a location on the shaft structure 20 (as indicated by arrow 32). The needle driver device 10 has a needle actuator in the form of a plunger 40 which may be reciprocated as indicated by arrow 42. In the embodiment of FIG. 1, the plunger 40 has a rack 43 and a pinion gear 44 which are used to reciprocate the plunger. The plunger 40 is coupled to the pinion gear 44 which is rotated when trigger 46 is squeezed. In this embodiment, the gear 44 may be used in a fashion similar to rack and pinion to drive or reciprocate the plunger 40. As will be described below, movement of the plunger 40 will be used to deliver needles into the suture organizer 30. Sutures S are typically coupled to the needles. The device 10 is used to deliver one end of the suture S into the body duct B, while the other end of the suture S may be delivered into another targeted tissue structure using a needle drive attached to the other end of the device 10 (as indicated in phantom) or by using an altogether separate device or method to connect the end of the suture to the targeted tissue.

Figure 2:
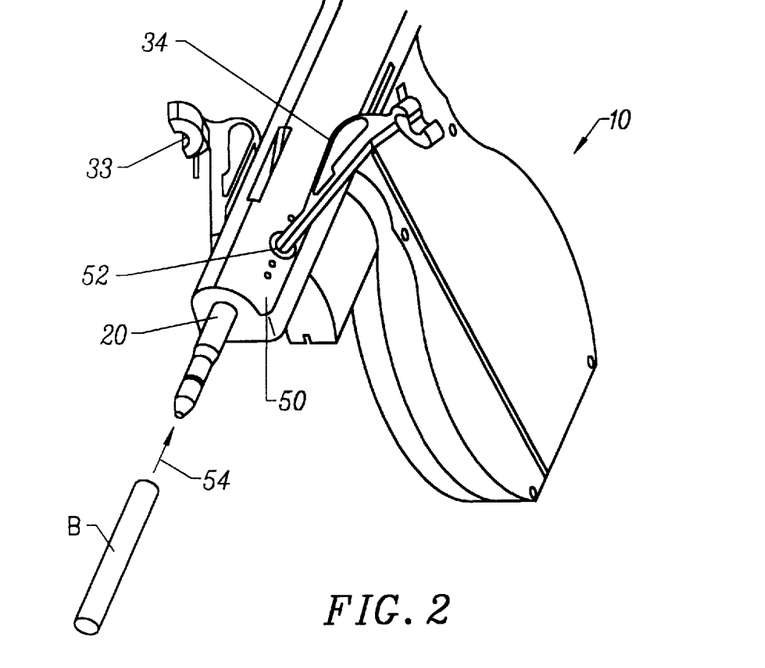
FIGS. 2 through 4 provide perspective views of the apparatus in FIG. 1 when it is used to deliver sutures through a body duct.
Figure 3:
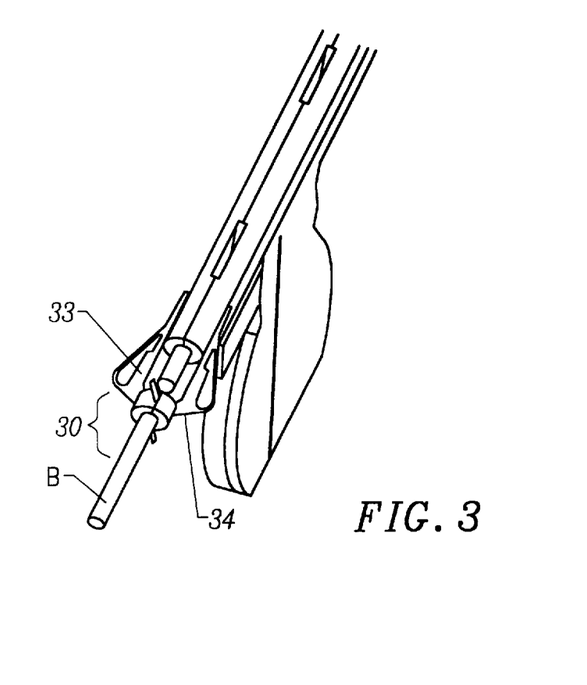
Figure 4:
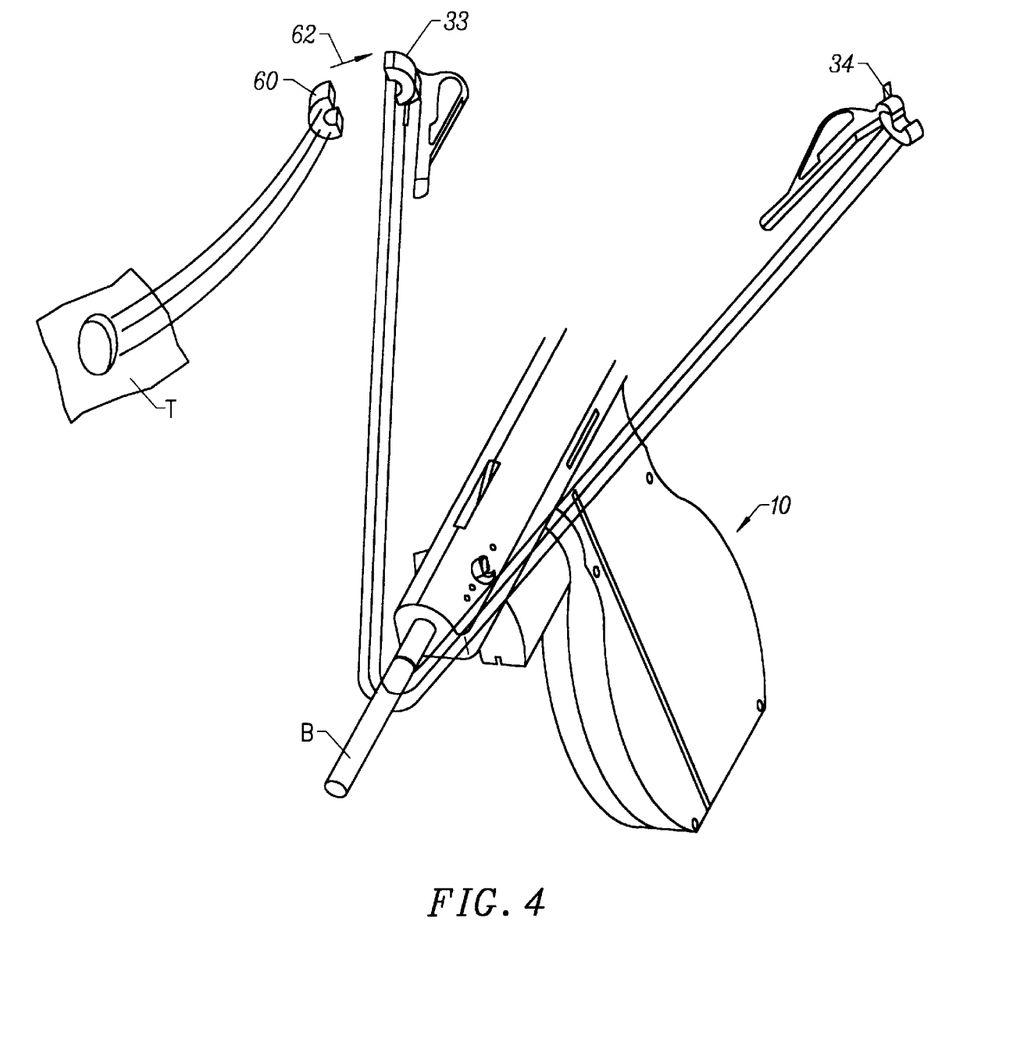

FIGS. 2 through 4 will now illustrate the use of device 10 to deploy sutures S through a body duct B. Referring now to FIG. 2, in this embodiment of the needle driver device 10, the suture organizer 30 may be divided into a first breakaway portion 33 and a second breakaway portion 34 which may be held in a retracted position as shown in FIG. 2. The suture organizer portions 33 and 34 are preferably pivotally mounted to the housing 50 of the device 10 through a ball socket 52. The housing 50 as shown in FIG. 1. has a pistol grip configuration. Of course, the suture organizer 30 may also be mounted at various other locations on the device such as on the shaft structure 20 for example. The body duct B is advanced onto the shaft structure 20 as indicated by arrow 54.

Referring now to FIG. 3, after the body duct B is properly positioned over the shaft structure 20, the suture organizer 30 is moved into a needle receiving position about the body duct. The position of the body duct B over the shaft structure 20 may be used to determine how far in from the end of the body duct the sutures are positioned. Typically, needles enter the body duct B about 0.5 mm to 2 mm from the proximal end of the duct. The suture organizer 30 may be used to clamp the body duct B onto the shaft structure. Of course in some embodiments, the suture organizer 30 may also be located about the body duct without contacting the body duct. As will be shown more clearly in FIGS. 5 and 6, needles are delivered in a radially outward direction from the shaft structure 20 and outwardly through the body duct into the suture organizer 30. The suture organizer 30 preferably, but not necessarily, holds the needles in a fixed configuration relative to one another which will organize the sutures to be tied off individually. Typically, one portion of the suture organizer 30 holds about half of the needles in the fixed configuration while second portion of the suture organizer 30 holds the other half of the needles in a fixed configuration.

As seen in FIG. 4, portions 33 and 34 of the suture organizer 30 may be removed from the needle driver 10. With the suture organizer 30 disconnected, the breakaway portions 33 and 34 may be used to draw the sutures away from the body duct B. Of course, the suture organizer 30 may also be moved away from the needle receiving position without having to be disconnected from the needle driver 10. As seen in FIG. 4, another suture organizer 60, which may be a suture organizer from another needle driver device, may be coupled to suture organizer 30 as indicated by arrow 62. The organizers 30 and 60 preferably have a surface adapted to engage one another. In some embodiments, the other suture organizer 60 may be carrying the ends of sutures which are coupled to a target tissue T. They may be the other end of the sutures held in the suture organizer 30. Mating the suture organizer 60 with the suture organizer 30 will organize and align opposite ends of individual sutures to facilitate the tying off of the sutures.

Figure 5:
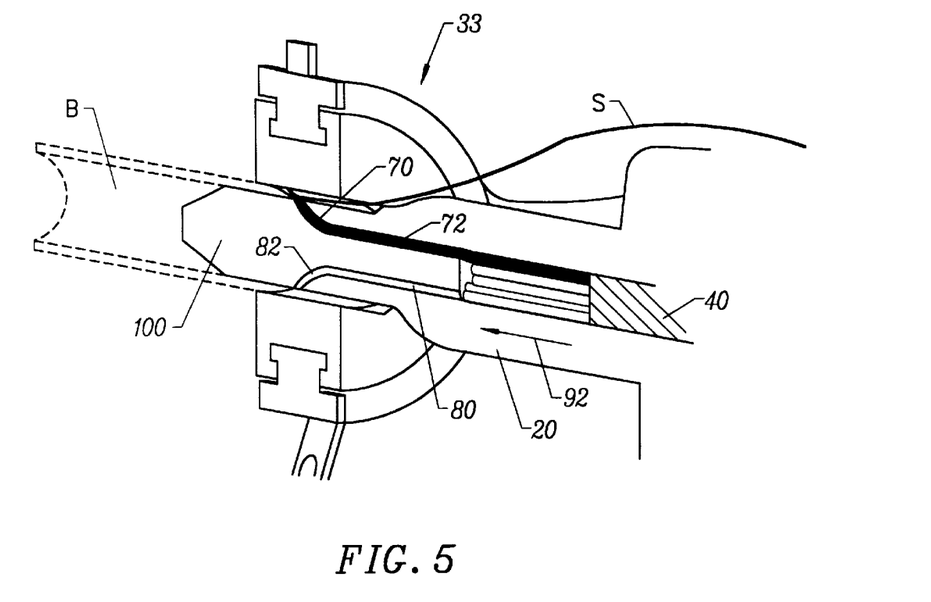
FIGS. 5 through 6 are cross-sectional views of the distal end of the apparatus in FIG. 1 showing the delivery of a needle into a suture organizer.
Figure 6:
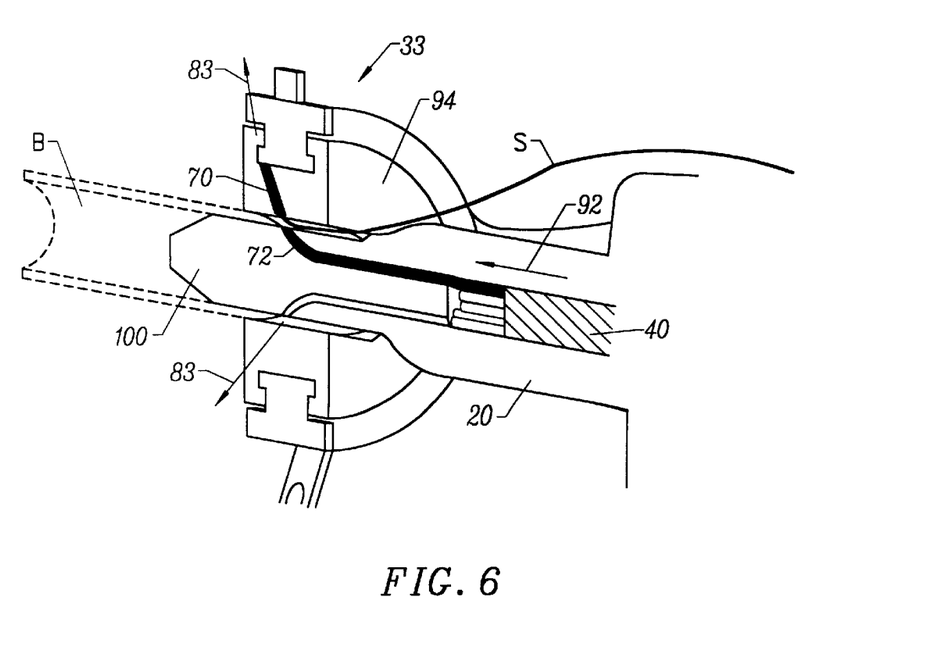

Referring now to FIGS. 5 and 6, needle delivery using the device 10 will be described in further detail. FIG. 5 shows a cross-section of the shaft structure 20 with the first breakaway portion 33 of the suture organizer mounted in a needle receiving position about the body duct B. For ease of illustration, only one needle 70 and push rod 72 is shown in the device. It should be understood that a preferred embodiment of the device 10 includes a plurality of needles 70 and push rods 72. Typically, the needles 70 and push rods 72 are made of superelastic material such as a nickel-titanium alloy which can traverse a curved channel 80. The body duct B shown in phantom is mounted between the shaft structure 20 and portion 34 of the suture organizer 30. The needle 70 and push rod 72 are positioned in the needle guide channel 80, and the guide channels 80 are spaced to deliver the needles in an evenly spaced radial pattern (i.e., spaced peripherally apart by generally equal distances, typically 1 mm to 2 mm). In some embodiments, these needle guides may comprise tubes or other devices for guiding the needles. As seen in FIG. 5, the channel 80 has a curved portion 82 which directs the needles outwardly towards the body duct B. In some embodiments, the push rod 72 extends to the plunger 40 (more clearly illustrated in FIG. 9) and may be moved in the direction indicated by arrow 92.

As seen in FIG. 6, the push rod 72 will deliver the needle 70 in a radially outward direction as indicated by arrow 83 into a soft material insert 94 in breakaway portion 33 of the suture organizer 30. Preferably, the needle 70 is substantially, more preferably fully, embedded into the soft material insert 94 after being advanced. The material insert 94 may be a polymer or a silicone material, which has sufficient compressive strength to retain the needle 70 in the suture organizer. Preferably, but not necessarily, shorter needles 70 preferably between the range of about 3 mm to 6 mm are used in the device so that they may be more easily retained in the suture organizer. Although longer needles may be used, of course, the shorter needles, as shown in FIG. 6, facilitate the removal of the suture organizer 30 by staying within the organizer and not pulling out. The sutures S attached to the needles are typically, but not necessarily, attached to the distal tip of the needle. This facilitates loading of the needle 70 into the needle guide channel of the shaft structure 20 since the suture S does not need to be loaded completely into the channel 80. As seen in FIGS. 5 and 6, the sutures S typically extend towards a proximal end of the device 10 to facilitate the suturing process. The sutures S may also be positioned to extend towards a distal end of the body duct B.

To facilitate manufacturing, a preferred embodiment of the device 10 has a distal mating portion 100 having a plurality of radial grooves which are used to define the needle guide channel 80. The insert 100 is received into a lumen of the shaft 20 which is the proximal mating portion. Although the channels may be integrally formed in the shaft structure 20, drilled or otherwise formed within the shaft structure, using a multi-piece device where one of the pieces has a surface with grooves and facilitates the manufacture of the device by eliminating the need for the more expensive forming or drilling steps. For example, the grooves could be formed on a proximal, tapered surface of the insert 100 and/or on the distal, interior surface of the main shaft 20. In all cases, the grooves would form the desired needle-guiding channels when the insert 100 is attached to the shaft 20. Such fabrication techniques not only simplify construction but also permit the fabrication of smaller diameter devices.

Figure 7:
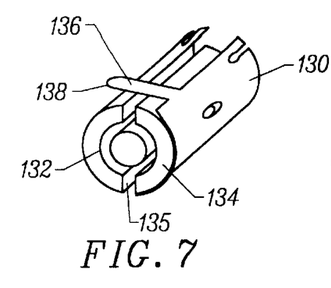
FIGS. 7 through 8 show various views of one embodiment of the suture organizer.
Figure 8:
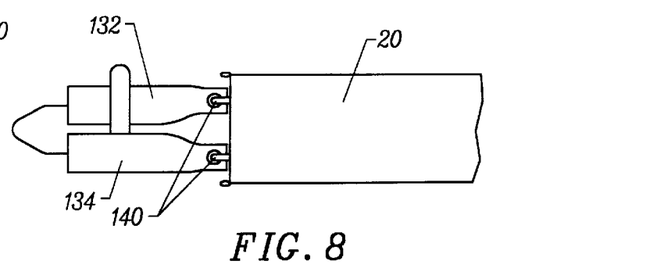

Referring now to FIGS. 7 and 8, another embodiment of the suture organizer will now be described. As seen in FIG. 7, suture organizer 130 has a first breakaway portion 132 and a second breakaway portion 134. Each portion has a surface 135 adapted to mate with another suture organizer portion. A tab 136 having ratchet teeth 138 may be used to hold portions 132 and 134 together. As seen in FIG. 8, the portions 132 and 134 are attached to the shaft structure 20 with ball joints 140. These hinges are located closer to the distal end of the shaft 20 wherein the suture organizer 30, as shown in FIG. 2, has ball joints located further from the distal end. The ball joints in FIG. 8 allow the portions to be separated and easily removed from the shaft structure 20. Aside from the ratchet tab 134, a variety of other attachment devices may be used to secure the portions 132 and 134 together in a releasable manner.

Figure 9:
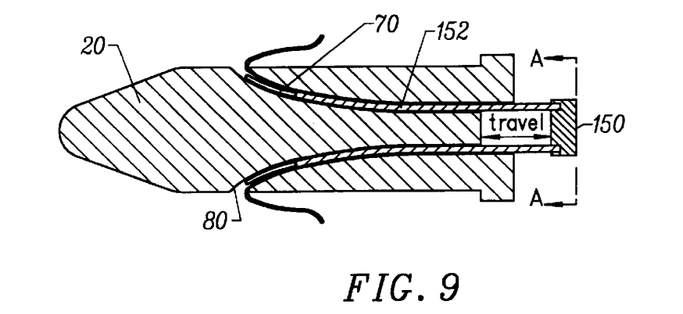
FIGS. 9 through 10 are cross-sectional views of a distal end of the apparatus according to the present invention showing a variety of needle guide channels.
Figure 10:
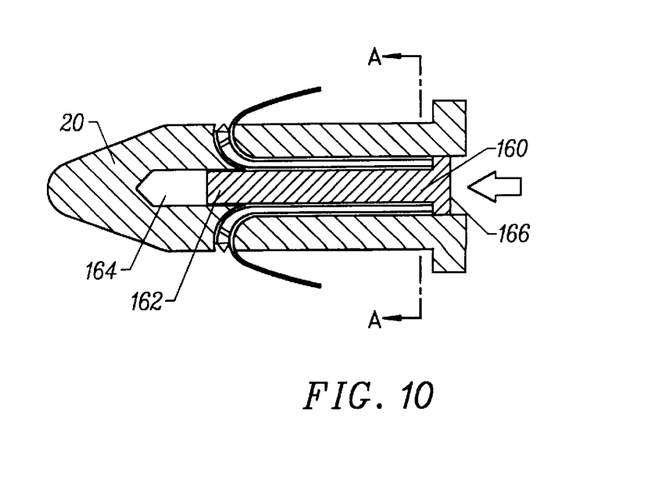
Figure 11:
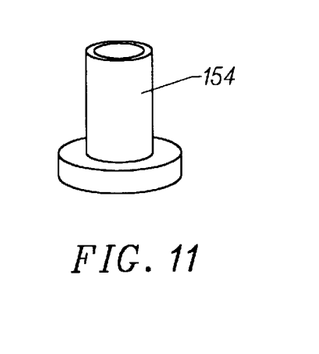
FIGS. 11 through 12 show embodiments of a drive shaft used with the present invention.
Figure 12:
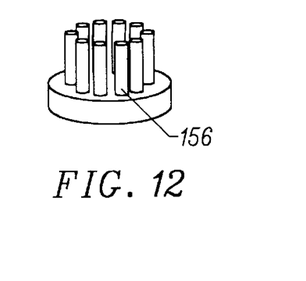

Referring now to FIGS. 9 through 12, the actuating shaft used in the shaft structure 20 will be described in further detail. As seen in FIG. 9, small needles 70 are typically used with the needle driving device 10. The needle actuator 150 has an elongate portion 152 which can advance the needle 70 out of the channels 80 in the shaft structure 20. Preferably, the needles can be completely advanced from the needle guide channel 80. Depending on the shape of the channels 80, the elongate portion 152 of the needle actuator 150 may use a cylindrical structure 154 as shown in FIG. 11 or have a plurality of push rods 156 as shown in FIG. 12. The push rods 156 are preferably made of a superelastic material such as a nickel-titanium alloy which can traverse the curved channel 80. FIG. 10 shows an alternative embodiment where the actuating member 160 has a center portion 162 which is received by lumen 164 in the shaft structure 20. As the actuating member 160 is advanced, the lips 166 will push the needles from the needle guide channels 80.

Figure 13:
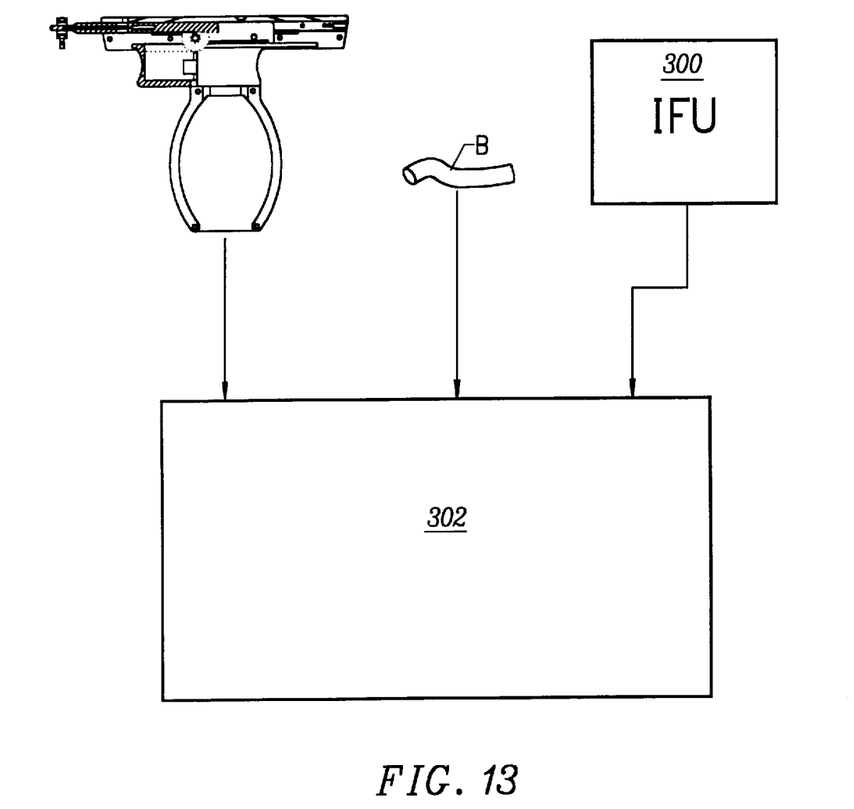
FIG. 13 shows a kit according to the present invention.
Figure 14:
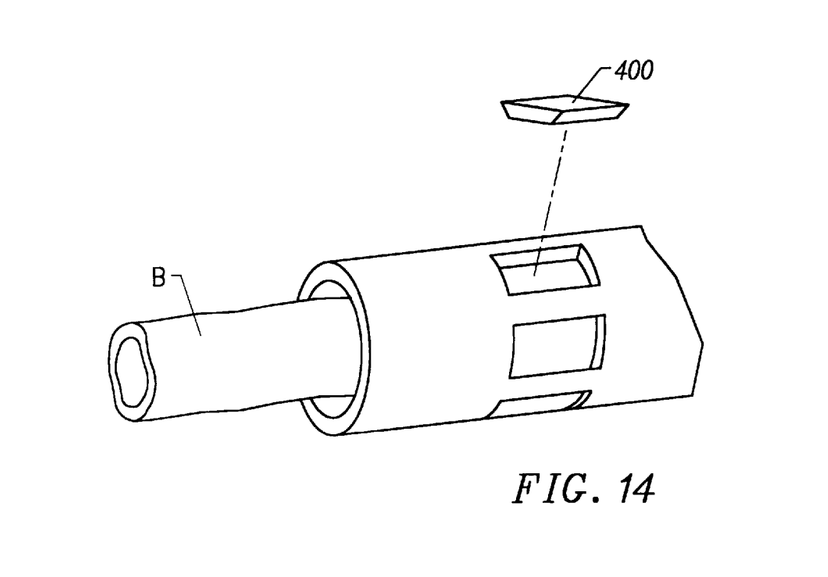
FIG. 14 shows an alternative embodiment of the suture organizer according to the present invention.

Referring now to FIG. 13, the suturing device 10 of the present invention will usually be packaged in kits. In addition to the suturing device 10, such kits will include at least instructions for use 300 (IFU). The suturing device and instructions for use will usually be packaged together within a single enclosure, such as a pouch, tray, box, tube, or the like 302. In alternative embodiments, the kit may also include the body duct B to be sutured to a target vessel or other accessories such as sutures and additional needles. Such body ducts B are typically artificial or synthetic grafts. At least some of the components may be sterilized within the container. Instructions for use 300 will set forth any of the methods described above.

While all the above is a complete description of the preferred embodiments of the inventions, various alternatives, modifications, and equivalents may be used. For example, the shaft structure may have markings such as grooves, texturing, or visible stripping to facilitate positioning of the graft body duct on the shaft structure. The device may be adapted for use with other anastomosis devices such as the device described in commonly assigned, copending application Ser. No. 09/395,901 filed on Sep. 14, 1999, the full disclosure of which is incorporated herein by reference. Of course, the device may also be used to deliver needles or other body duct connectors which are not carrying sutures but include other connecting devices. Additionally, the suture organizer may be divided into more than just one or two portions. The suture organizer may have three, four, or five, or any number of portions in these alternative embodiments. These portions of the suture organizer may also be partially contained in a housing or other structure which may surround the body duct. For example, the body duct may be contained or otherwise mounted on a cylindrical housing surrounding the body duct. As illustrated in FIG. 13, the housing may have a plurality of openings in the side wall, where these openings may each contain a portion 400 of the suture organizer which may be removed to pull sutures away from the body duct. These portions may be press-fit, clamped, or otherwise held in the openings on the housing. Although the foregoing invention has been described in detail for purposes of clarity of understanding, it will be obvious that certain modifications may be practiced within the scope of the appended claims.

What is claimed is:

1. A needle driver for use with a body duct, the needle driver comprising:

a shaft structure having a portion which holds an end of the body duct;

a suture organizer mounted about said portion of the shaft structure; and a plurality of needles on the shaft structure, wherein each of said needles is arranged to be advanced along a path to carry suture in radially outward direction from the shaft structure through said body duct and into said suture organizer.

2. A device as in claim 1, wherein said shaft structure comprises a plurality of needle guides for directing said needles longitudinally along the shaft structure and then radially outward from the shaft structure.

3. A device as in claim 2, wherein said needle guides comprise a plurality of needle guide channels in said shaft structure.

4. A device as in claim 3, wherein each of said needle guide channels includes a curved portion directing said needles outwardly from the shaft structure towards the body duct when said needles are advanced.

5. A device as in claim 3, wherein each of said needle guide channels forms a J-shaped path.

6. A device as in claim 1, wherein said shaft structure comprises a distal mating portion and a proximal mating portion, wherein said distal mating portion is partially mounted within a lumen of the second mating portion to define needle guides.

7. A device as in claim 1, further comprising a needle actuator for simultaneously advancing said plurality of needles from the shaft structure, through the body duct, and into the suture organizer.

8. A device as in claim 7, wherein said needle actuator comprises a plurality of push rods for engaging and advancing said needles.

9. A device as in claim 7, wherein said needle actuator comprises a plunger having a rack coupled to a pinion which rotates to move said plunger.

10. A device as in claim 1, wherein said shaft structure includes a pistol grip housing.

11. A device as in claim 1, wherein said suture organizer is adapted to mate with another suture organizer.

12. A device as in claim 11, wherein said suture organizer is removably secured to the shaft structure.

13. A device as in claim 11, wherein said suture organizer comprises a first breakaway portion and a second breakaway portion to facilitate removal of the suture organizer from the body duct.

14. A device as in claim 11, wherein the suture organizer comprises a plurality of portions adapted to be mounted about the body duct graft wherein each of said portions has a releasable connection with the device so that the portions may be removed for pulling sutures away from the body duct.

15. A device as in claim 1, wherein the suture organizer is adapted to hold said needles after the needles are removed from the shaft structure.

16. A device as in claim 15, wherein the suture organizer comprises a polymeric material for receiving and holding needles inserted therein.

17. A device as in claim 16, wherein said polymeric material has a thickness sufficient to substantially contain said needles therein.

18. A device as in claim 1, wherein the suture organizer has a cylindrical configuration when mounted radially about said tubular portion of the body duct.

19. A device as in claim 1, wherein the suture organizer further comprises an arm pivotally coupling a portion of the suture organizer to the device.

20. A device as in claim 1, wherein said plurality of needles are arranged in an evenly spaced radial pattern about said shaft structure.

21. A device as in claim 1, wherein each of said plurality of needles carries a suture having a suture end.

22. A device as in claim 1, wherein said plurality of needles comprise a superelastic material.

23. A device as in claim 1, wherein said plurality of needles each have a length in the range from 3 mm to 6 mm.

24. A method for penetrating a plurality of first suture ends through a body duct, the method comprising:

positioning an end of the body duct over a shaft structure;

advancing a plurality of needles carrying a plurality of sutures having said first sutures ends in a radially outward direction from the shaft structure through the end of the body duct, and into a suture organizer, wherein the suture ends are captured by the suture organizer; and moving said suture organizer relative to the shaft structure to draw said first suture ends away the body duct.

25. A method as in claim 24 further comprising mating said suture organizer to another suture organizer having a plurality of second suture ends to facilitate the tying off of said first and second suture ends.

26. A method as in claim 25, wherein said second suture ends are on said plurality of sutures having said first suture ends.

27. A method as in claim 25, wherein said tying off of said first and second suture ends brings said body duct in contact with a target tissue.

28. A method as in claim 25, further comprising mapping said suture ends coupled to said needles in said suture organizer to suture ends on said another suture organizer.

29. A method as in claim 24 further comprising maintaining said needles in a substantially fixed configuration by the suture organizer after the needles are removed from the shaft structure.

30. A method as in claim 24, wherein said positioning step comprises clamping said body duct to the shaft structure with the suture organizer.

31. A method as in claim 24, wherein said advancing of said needles includes advancing a needle actuator to move said plurality of needles through needle channels in said shaft structure.

32. A method as in claim 24, wherein advancing of said needles embeds said needles in the suture organizer, said suture organizer retaining said needles after said needles have been removed from the shaft structure.

33. A method as in claim 24, wherein said needles are advanced into a suture organizer mounted in a needle receiving position about the body duct.

34. A method as in claim 24, wherein said moving step comprises separating said suture organizer into a first breakaway portion and a second breakaway portion each having a surface adapted to mate with another suture organizer.

35. A method as in claim 24, wherein said moving step comprises moving a plurality of suture organizer portions relative to the shaft structure.

36. A method as in claim 24, wherein said needles are advanced in a evenly spaced radial pattern through the body duct.

37. A kit comprising:

a suturing device adapted to deliver a plurality of needles;

instructions for use in placing a plurality of suture ends through a body duct wherein the instructions comprise positioning an end of the body duct over a shaft structure, advancing a plurality of needles carrying sutures with said suture ends, each of said needles advancing in a radially outward direction from the shaft structure through the end of the body duct and into a suture organizer, and moving said suture organizer to draw said sutures away from the body duct; and a package adapted to contain the device and the instructions for use.

38. A kit as in claim 37, wherein said instructions for moving said suture organizer further comprises mating said suture organizer with another suture organizer.

39. A method for suturing tissue locations together, said method comprising:

providing a plurality of suture lengths, wherein each suture length has a first end and a second end;

penetrating the first ends of the suture lengths in a predetermined pattern at a first tissue location;

capturing the first suture ends in a first suture organizer;

penetrating the second ends of the suture lengths in a pre-determined pattern at a second tissue location;

capturing the second suture ends in a second suture organizer;

positioning the first suture organizer relative to the second suture organizer; and securing the first and second ends of at least some of the suture lengths.

* * * * *